United States Patent [19]

Lindel et al.

[11] Patent Number: 4,927,938

[45] Date of Patent: May 22, 1990

[54] HALOGEN SUBSTITUTED PYRIDYLALKYL KETONES

[75] Inventors: Hans Lindel, Leverkusen; Werner Hallenbach, Langenfeld, both of Fed. Rep. of Germany

[73] Assignee: Bayer Aktiengesellschaft, Leverkusen, Fed. Rep. of Germany

[21] Appl. No.: 215,683

[22] Filed: Jul. 6, 1988

[30] Foreign Application Priority Data

Jul. 11, 1987 [DE] Fed. Rep. of Germany ....... 3723070

[51] Int. Cl.[5] .......................................... C07D 213/50
[52] U.S. Cl. ..................................................... 546/315
[58] Field of Search ........................................ 546/315

[56] References Cited

U.S. PATENT DOCUMENTS

| 3,646,042 | 2/1972 | Krenzer et al. | 546/315 |
| 4,018,910 | 4/1977 | Winter et al. | 546/315 |
| 4,045,446 | 8/1977 | Wu et al. | 546/315 |

FOREIGN PATENT DOCUMENTS

| 3615293 | 11/1987 | Fed. Rep. of Germany . | |
| 2238264 | 4/1986 | Japan | 546/315 |

Primary Examiner—Mary C. Lee
Assistant Examiner—Catherine S. Kilby Scalzo
Attorney, Agent, or Firm—Sprung Horn Kramer & Woods

[57] ABSTRACT

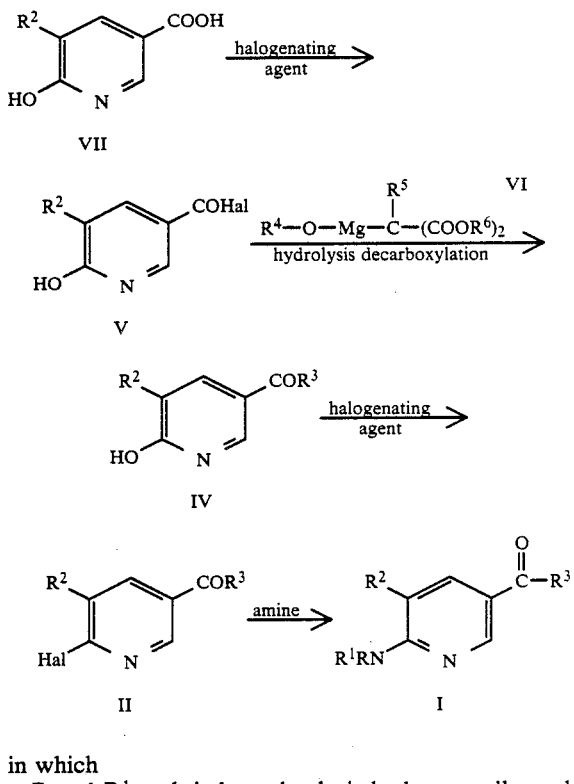

in which
R and $R^1$ each independently is hydrogen, alkanoyl or alkyl or, together with the adjacent nitrogen atom, form an optionally substituted saturated or unsaturated heterocyclic radical,
$R^2$ is halogen,
$R^3$ is alkyl,
$R^4$ is $C_{1-3}$-alkyl,
$R^5$ is hydrogen or $C_{1-2}$-alkyl,
$R^6$ is $C_{1-3}$-alkyl, and
Hal is halogen.

The process is new as are intermediates II, IV and V. The products are known intermediates.

1 Claim, No Drawings

HALOGEN SUBSTITUTED PYRIDYLALKYL KETONES

The present invention relates to a new process for the preparation of substituted pyridylalkyl ketones, intermediate products for carrying out this process and their preparation.

Pyridylalkyl ketones and their use as intermediate products for the preparation of pyridylethanolamines are described in application Ser. No. 040,509, filed Apr. 20, 1987, now pending, corresponding to German Patent Application No. P 3 615 293.5.

By the process described therein, they are obtained by reacting nicotinic acid alkyl esters with acetic acid alkyl esters in a Claisen ester condensation and the pyridoylacetic acid esters thus obtained are hydrolyzed and decarboxylated.

The pyridylethanolamines are active compounds for promoting the yield of animals.

The following have now been found: 1. Process for the preparation of pyridylalkyl ketones of the formula (I)

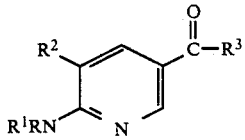

in which

R and $R^1$ independently of one another represent hydrogen, alkanoyl or alkyl or, together with the adjacent nitrogen atom, form an optionally substituted saturated or unsaturated heterocyclic radical, $R^2$ represents halogen and $R^3$ represents alkyl, which is characterized in that compounds of the formula (II)

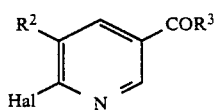

in which $R^2$ and $R^3$ have the above-mentioned meaning and Hal represents halogen, are reacted with amines of the formula (III)

H—NR $R^1$ (III)

in which

R and $R^1$ have the abovementioned meaning. 2. The compounds of the formula (II)

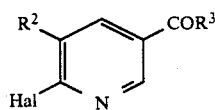

in which

Hal and $R^2$ represent halogen and $R^3$ represents alkyl, are new. 3. Process for the preparation of the compounds of the formula (II)

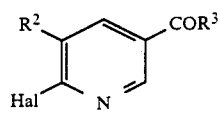

in which

Hal, $R^2$ and $R^3$ have the abovementioned meaning, which is characterized in that compounds of the formula (IV)

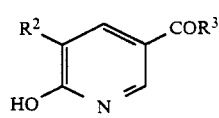

in which $R^2$ and $R^3$ have the abovementioned meaning, are halogenated. 4. The compounds of the formula (IV)

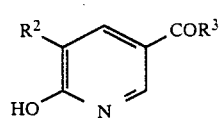

in which $R^2$ and $R^3$ have the meaning given in the case of the compounds of the formula (I), are new. 5. Process for the preparation of the compounds of the formula (IV)

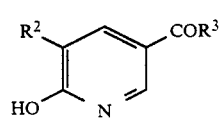

in which $R^2$ and $R^3$ have the abovementioned meaning, characterized in that compounds of the formula (V)

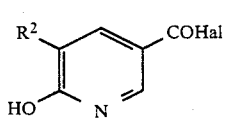

in which $R^2$ has the abovementioned meaning and

Hal represents halogen, are reacted with compounds of the formula (VI)

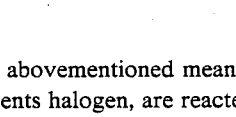

$$R^4-O-Mg-\underset{\underset{R^5}{|}}{C}-(COOR^6)_2 \quad (VI)$$

in which $R^4$ represents $C_{1-3}$-alkyl, $R^5$ represents hydrogen or $C_{1-2}$-alkyl and $R^6$ represents $C_{1-3}$-alkyl, and the products are then hydrolyzed and decarboxylated. 6. The compounds of the formula (V)

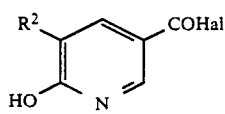 (V)

in which

Hal and R² represent halogen, are new. 7. Process for the preparation of the compounds of the formula (V)

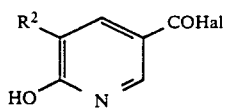 (V)

in which

Hal and R² represent halogen, characterized in that compounds of the formula (VII)

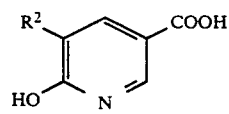 (VII)

in which

R² represents halogen, are reacted with halogenating agents.

Compounds of the formula (I) which are preferably prepared by the new processes are those in which R represents hydrogen or $C_1$-$C_3$-alkyl, R¹ represents hydrogen, $C_1$-$C_3$-alkyl or $C_1$-$C_3$-alkanoyl, or R and R¹, together with the nitrogen atom to which they are bonded, represent a heterocyclic radical, R² represents chlorine or bromine and R³ represents methyl or ethyl.

Compounds of the formula (I) which are particularly preferably prepared are those in which R represents hydrogen or methyl, R¹ represents hydrogen, methyl or acetyl, or R and R¹, together with the nitrogen atom, represent a 5- or 6-membered ring which optionally contains further hetero atoms, such as pyrrolidonyl, pyrryl, piperidinyl or morpholinyl, R² represents chlorine and R³ represents methyl or ethyl.

The compounds of the formula (I) in which at least one of the radicals R and R¹ represents hydrogen can also exist in the following tautomeric forms:

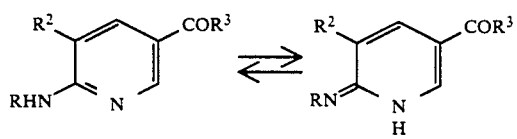

The following compounds of the formula (I) may be mentioned specifically: 2-amino-3-chloro-5-acetylpyridine, 2-amino-3-chloro-5-propionylpyridine, 2-amino-3-bromo-5-acetylpyridine, 2-amino-3-bromo-5-propionylpyridine, 2-methylamino-3-chloro-5-acetylpyridine, 2-acetylamino-3-chloro-5-acetylpyridine, 2-acetylamino-3-bromo-5-acetylpyridine, 2-(N-pyrrolo)-3-chloro-5-acetylpyridine and 2-(N-morpholino)-3-chloro-5-acetylpyridine.

If, in process (1), 2,3-dibromo-5-propionylpyridine is used as the compound of the formula (II) and methylamine is used as the amine of the formula (III), the process can be represented by the following equation:

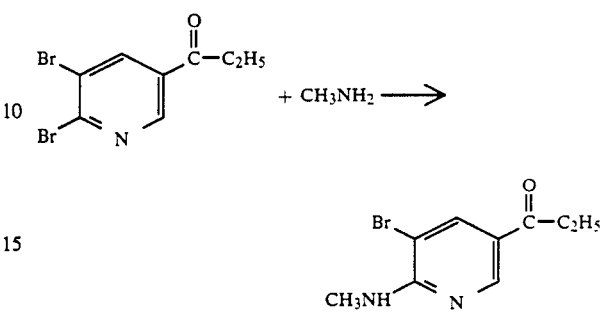

Amines of the formula (III) are known. Amines of the formula (III) in which R and R¹ have the meanings given as preferred in the case of the compounds of the formula (I) are preferred. The following amines of the formula (III) may be mentioned specifically: ammonia, methylamine, ethylamine, n- and iso-propylamine, dimethylamine, diethylamine, methylethylamine, pyrrole, pyrrolidine, piperidine, morpholine, methylaniline and ethylaniline.

Compounds of the formula (II) are new. They are prepared by the process described below. Compounds of the formula (II) in which R² and R³ have the meanings given as preferred in the case of the compounds of the formula (I) and Hal represents chlorine or bromine are preferred.

Compounds which may be mentioned specifically are: 2,3-dichloro-5-acetylpyridine, 2,3-dichloro-5-propionylpyridine, 2-chloro-3-bromo-5-acetylpyridine, 2-chloro-3-bromo-5-propionylpyridine, 2,3-dibromo-5-propionylpyridine and 2,3-dibromo-5-acetylpyridine.

Process (1) is carried out by reacting the compound of the formula (II) with 2 to 5 times, preferably 2 to 3 times, the molar amount of amine of the formula (III), if appropriate in a diluent.

Diluents which can be used are all the inert organic solvents. These include, in particular, optionally halogenated aliphatic or aromatic hydrocarbons, such as pentane, hexane, heptane, cyclohexane, benzene, toluene, methylene chloride, chloroform, dichloroethane and chlorobenzene, and furthermore ethers, such as diethyl ether, tetrahydrofuran or dioxane, as well as amides, such as dimethylformamide, and water.

The reaction is carried out at temperatures from 20° C. to 250° C.

The reaction is carried out at normal pressure or under increased pressure.

If, in process (3), 2-hydroxy-3-bromo-5-propionylpyridine is used as the compound of the formula (IV), the process can be represented by the following equation:

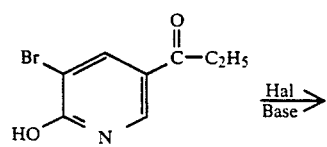

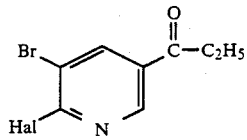

The compounds of the formula (IV) are new. They are prepared by the process described below. The substituents $R^2$ and $R^3$ preferably have the meanings given as preferred in the case of the compounds of the formula (I). The following compounds of the formula (IV) may be mentioned specifically: 2-hydroxy-3-chloro-5-acetylpyridine, 2-hydroxy-3-chloro-5-propionylpyridine, 2-hydroxy-3-bromo-5-acetylpyridine and 2-hydroxy-3-bromo-5-propionylpyridine.

Process (3) is carried out by reacting a compound of the formula (IV) with about the equimolar amount of a halogenating agent in the presence of the equimolar amount of an auxiliary base in a diluent. Diluents which can be used are all the inert organic solvents. These include optionally halogenated aliphatic or aromatic hydrocarbons, such as pentane, hexane, heptane, cyclohexane, benzene, toluene, methylene chloride, chloroform, dichloroethane, chlorobenzene and dichlorobenzene; and furthermore ethers, such as diethyl ether and tetrahydrofuran.

The halogenating agents used are preferably phosphorus oxyhalides, such as phosphorus oxychloride and phosphorus oxybromide, as well as phosgene.

The auxiliary bases used in the reaction are tertiary amines, such as trialkylamines, dialkylarylamines, alkyldiarylamines and pyridine.

The reaction is carried out at temperatures from 20° C. to 200° C., preferably at 50° C. to 150° C.

The reaction is carried out under normal pressure or increased pressure.

If, in process (5), 5-bromo-6-hydroxynicotinoyl chloride is used as the compound of the formula (V) and dimethyl methoxymagnesiummalonate is used as the compound of the formula (VI), process (5) can be represented by the following equation:

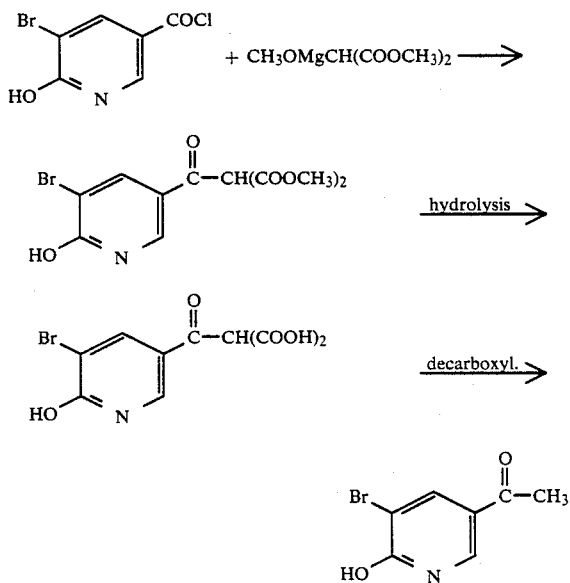

Compounds of the formula (V) are new. Their preparation is described below. The substituents $R^2$ and Hal preferably have the meanings given above. The following compounds of the formula (V) may be mentioned specifically: 5-bromo-6-hydroxynicotinoyl chloride and 5-chloro-6-hydroxynicotinoyl chloride.

Compounds of the formula (VI) are known (Org. Synth. Coll. Vol. IV (1963), 285; and Ber. Dt. Chem. Ges. 67 (1934), 935).

The following compounds of the formula (VI) may be mentioned specifically: dimethyl methoxymagnesiummalonate, diethyl ethoxymagnesiummalonate and diethyl ethoxymagnesiummethylmalonate.

The process is carried out by reacting equimolar amounts of the compounds of the formulae (V) and (VI) in a diluent and then hydrolysing the product, the β-ketodicarboxylic acid being decarboxylated. Diluents used are all the inert organic solvents. These include optionally halogenated aliphatic and aromatic hydrocarbons, such as pentane, hexane, benzene, toluene, methylene chloride, chloroform and chlorobenzene; ethers, such as diethyl ether and tetrahydrofurane and alcohols, such as methanol and ethanol. The reaction is carried out at temperatures from 20° C. to 150° C., preferably at the boiling point of the solvent used.

The hydrolysis is carried out with inorganic acids, such as hydrochloric acid or sulphuric acid, or organic carboxylic acids, such as acetic acid or propionic acid. It is also possible to use mixtures of inorganic and organic acids. Hydrolysis with alcoholic and aqueous solutions of bases, such as alkali metal hydroxides and alkaline earth metal hydroxides, carbonates and bicarbonates, is also possible. Bases which may be mentioned specifically are: sodium, potassium and barium hydroxide and sodium and potassium carbonate.

If, in process (7), 5-bromo-6-hydroxy-nicotinic acid is used as the carboxylic acid of the formula (VII) and thionyl chloride is used as the halogenating agent, the reaction can be represented by the following equation:

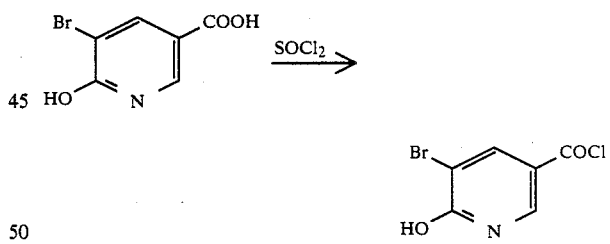

The compounds of the formula (VII) are known (European Published Specification No. 136,593). Compounds of the formula (VII) in which $R^2$ represents chlorine or bromine are preferred.

The halogenating agents used are inorganic acid chlorides. Examples which may be mentioned are: phosphorus oxychloride, phosphorus pentachloride and thionyl chloride.

The reaction is carried out by treating a substituted nicotinic acid of the formula (VII) with 0.1 to 1.5 equivalents of the inorganic acid chloride, if appropriate in a diluent.

The reaction is carried out at temperatures from 20° C. to 100° C., and is preferably carried out at normal pressure.

Diluents which can be used are all the inert organic solvents. These include, in particular, aliphatic and aromatic optionally halogenated hydrocarbons, such as pentane, hexane, cyclohexane, benzene, toluene, methylene chloride, chloroform and chlorobenzene; ethers, such as diethyl ether, tetrahydrofuran and dioxane, and phosphorus oxychloride.

The reaction is preferably carried out without a diluent.

The substituted pyridylalkyl ketones of the formula (I) obtainable by process (1) according to the invention are used for the preparation of pyridylethanolamine derivatives. For this, the acetylpyridines are reacted with elemental halogen or with copper halides. The halogenomethylpyridyl ketones thereby obtainable are then reduced and the pyridylhalogenoethanols thereby obtained are reacted with amines. This reaction can be illustrated by the following equation:

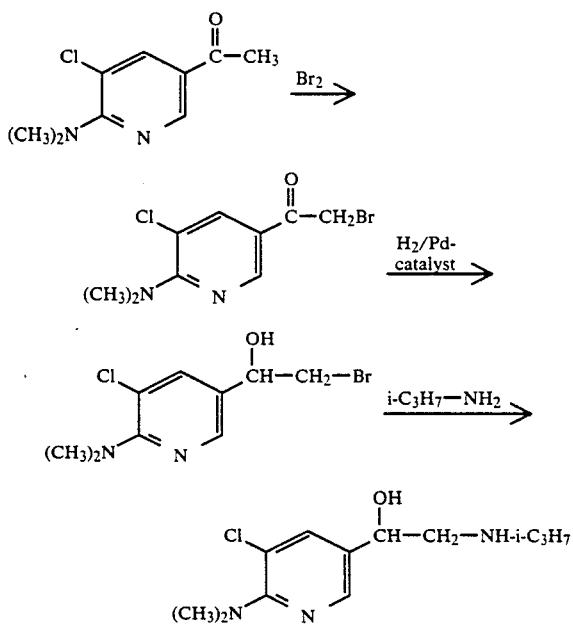

The halogenomethyl ketones can also first be reacted with amines and the products then reduced.

The procedure of these reactions is described in the above-mentioned Application Ser. No. 040,509, corresponding to German Patent Application No. P 3 615 293.5.

PREPARATION EXAMPLES

Example of process 1

EXAMPLE 1

2-Amino-3-chloro-5-acetylpyridine 1.9 g (10 mmol) of 2,3-dichloro-5-acetylpyridine are heated at 170° C. in a mixture of 80 ml of tetrahydrofuran and 20 ml of concentrated aqueous ammonia in an autoclave for 8 hours. After the tetrahydrofuran has been evaporated off, the residue is diluted with water and the mixture is brought to pH 5 and extracted with ethyl acetate.

Yield: 1.65 g (97%), melting point: 188° C.

Example of process 3

EXAMPLE 2

2,3-Dichloro-5-acetylpyridine 3.4 g (20 mmol) of 2-hydroxy-3-chloro-5-acetylpyridine are stirred with 3.7 g (24 mmol) of phosphorus oxychloride and 2.4 g (20 mmol) of N,N-dimethylaniline in 75 ml of chlorobenzene at 100° C. for 1.5 hours. The mixture is stirred into 200 ml of ice-water and extracted with ethyl acetate. Drying and evaporation gives 3.6 g (95%) of 2,3-dichloro-5-acetylpyridine, melting point: 80° C.

Example of process 5

EXAMPLE 3

2-Hydroxy-3-chloro-5-acetylpyridine 7.2 g (37.5 mmol) of 5-chloro-6-hydroxynicotinoyl chloride in 10 ml of absolute tetrahydrofuran are added to a boiling solution of 8.55 g (37.5 mmol) of diethyl ethoxymagnesium-malonate (prepared in accordance with Org. Synth. Coll. Vol. IV (1963), 285) in 120 ml of absolute tetrahydrofuran and the mixture is heated under reflux for 2 hours. After neutralization with 2N sulphuric acid, the organic phase is separated off and evaporated. The residue is heated under reflux in a mixture of 30 ml of glacial acetic acid, 20 ml of water and 5 ml of concentrated sulphuric acid for 4 hours. The mixture is stirred into ice-water, brought to pH 4 and extracted with ethyl acetate. Drying and evaporation gives 6 g (93%) of the title compound, melting point: 188° to 189° C.

Example of process 7

EXAMPLE 4

5-Chloro-6-hydroxynicotinoyl chloride 6.3 g (36 mmol) of 5-chloro-6-hydroxynicotinic acid are heated under reflux in 60 ml of thionyl chloride for 4 hours. After the volatile constituents have been stripped off, 50 ml of toluene are added and the mixture is evaporated again. Colorless crystals, yield 6.9 g (quantitative), melting point: >250° C.

Examples of further reaction of the substituted pyridylalkyl ketones to give substituted pyridylethanolamines Example a (Halogenation of the pyridylalkyl ketones)

2-Amino-3-chloro-5-pyridyl bromomethyl ketone 16 g (0.1 mol) of bromine are added dropwise to a solution of 17.05 g (0.1 mol) of 2-amino-3-chloro-5-acetylpyridine in a mixture of 19.3 g of hydrogen bromide (47% strength aqueous solution; 0.11 mol) and 500 ml of glacial acetic acid. The mixture is subsequently stirred for two hours, brought to pH 8 and extracted with ethyl acetate. Drying and evaporation gives 18.5 g (74%) of the title compound, melting point 134° C.

Example b (Reaction of the pyridylhalogenoalkyl ketones with amines)

2-Amino-3-chloro-5-pyridyl isopropylaminomethyl ketone 9.98 g (0.04 mol) of the compound prepared under Example a are introduced in portions into a solution of 11.8 g (0.2 mol) of isopropylamine in 150 ml of methanol at 0° C. The mixture is allowed to come to room temperature and is subsequently stirred for 2 hours and evaporated. The residue is taken up in buffer of pH 5 and washed with ether. The aqueous phase is brought to pH 9 and extracted with ethyl acetate. Drying and evaporation give 6.8 g (75%) of the title compound as an amorphous powder.

Example c (Reduction of the pyridylaminoalkyl ketones)

1-(2-Amino-3-chloro-5-pyridyl)-2-isopropylaminoethanol 0.38 g (10 mmol) of sodium borohydride is added in portions to a solution of 2.28 g (10 mmol) of the compound prepared according to Example b in 50 ml of methanol at 0° C. The mixture is allowed to come to room temperature and is brought to pH 1 with dilute hydrochloric acid and evaporated. The residue is taken up in water and the mixture is washed with ether. It is then brought to pH 10 and extracted with ethyl acetate. Drying and evaporation gives 2.1 g (92%) of the title compound, melting point 146° C.

The product is useful as an animal yield promoter as described in Application Ser. Np. 040,509, Supra.

It is understood that the specification and examples are illustrative but not limitative of the present invention and that other embodiments within the spirit and scope of the invention will suggest themselves to those skilled in the art.

We claim:

1. A compound of the formula

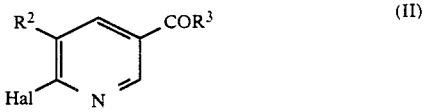

(II)

in which
Hal and $R^2$ each independently is halogen and $R^3$ is alkyl.

* * * * *